(12) United States Patent
Büchs et al.

(10) Patent No.: US 8,268,632 B2
(45) Date of Patent: Sep. 18, 2012

(54) METHOD AND DEVICE FOR RECORDING PROCESS PARAMATERS OF REACTION FLUIDS IN SEVERAL AGITATED MICROREACTORS

(75) Inventors: Jochen Büchs, Aachen (DE); Frank Kensy, Aachen (DE); Markus Samorski, Stuttgart (DE)

(73) Assignee: RWTH Aachen, Aachen (DE)

( * ) Notice: Subject to any disclaimer, the term of this patent is extended or adjusted under 35 U.S.C. 154(b) by 1483 days.

(21) Appl. No.: 11/547,021

(22) PCT Filed: Mar. 18, 2005

(86) PCT No.: PCT/EP2005/002928
§ 371 (c)(1),
(2), (4) Date: Sep. 29, 2006

(87) PCT Pub. No.: WO2005/098397
PCT Pub. Date: Oct. 20, 2005

(65) Prior Publication Data
US 2007/0256510 A1   Nov. 8, 2007

(30) Foreign Application Priority Data
Apr. 2, 2004   (DE) .......................... 10 2004 017 039

(51) Int. Cl.
*G01N 33/00* (2006.01)
*B01L 9/00* (2006.01)

(52) U.S. Cl. ........................ 436/165; 436/164; 73/865.3

(58) Field of Classification Search .................. 436/165, 436/164; 73/865.3; 356/427
See application file for complete search history.

(56) References Cited

U.S. PATENT DOCUMENTS

| | | | |
|---|---|---|---|
| 5,217,875 A | | 6/1993 | Karpf et al. |
| 5,325,295 A | * | 6/1994 | Fratantoni et al. ............ 356/427 |
| 5,372,936 A | | 12/1994 | Fraatz et al. |

(Continued)

FOREIGN PATENT DOCUMENTS

EP   0 353 592   2/1990

(Continued)

OTHER PUBLICATIONS

Gernot, John T. et al, Integratd Optical Sensing of Dissolved Oxygen in Microtiter Plates: A Novel Tool for Microbial Cultivation, Biotechnology and Bioengineering, vol. 81, No. 7, Mar. 30, 2003, pp. 829-836.*

*Primary Examiner* — Christine T Mui
(74) *Attorney, Agent, or Firm* — Lucas & Mercanti, LLP

(57) ABSTRACT

The invention relates to a method and a device for the recording of process parameters of reaction fluids in several microreactors which are continuously agitated, at least until the termination of the reaction in all the microreactors. The process parameters in the microreactor are recorded during the reaction by means of at least one sensor optical system. According to the invention, the reliability of the method may be increased, whereby, during the recording of the value of a process parameter, for example, on recording an instantaneous value of the auto-fluorescence of the reaction fluids, the sensor optical system is held stationary. The relative movement of the agitated microreactor and each sensor optical system thus produced is not problematical when the electromagnetic radiation from each sensor optical system is introduced exclusively into one of the microreactors concerned during the recording of the process parameter in said microreactor and the radiation emitted from the reaction fluid is only incident on the sensor of the corresponding sensor optical system.

25 Claims, 7 Drawing Sheets

U.S. PATENT DOCUMENTS 5,518,923 A    5/1996   Berndt et al.
7,122,321 B2  10/2006   Pantoliano et al.

FOREIGN PATENT DOCUMENTS

| | | | |
|---|---|---|---|
| EP | 0 448 923 | * | 10/1991 |
| EP | 0 677 732 | * | 10/1995 |
| JP | 47-41776 | | 12/1972 |
| JP | 61-188499 | | 11/1986 |
| JP | 2-78959 | | 3/1990 |
| JP | 8-205851 | | 8/1996 |
| JP | 9-508536 | | 9/1997 |
| JP | 2002-514571 | | 5/2002 |
| WO | WO 92/10754 | * | 6/1992 |
| WO | WO 96/39482 | | 12/1996 |
| WO | WO 99/24050 | | 5/1999 |

* cited by examiner

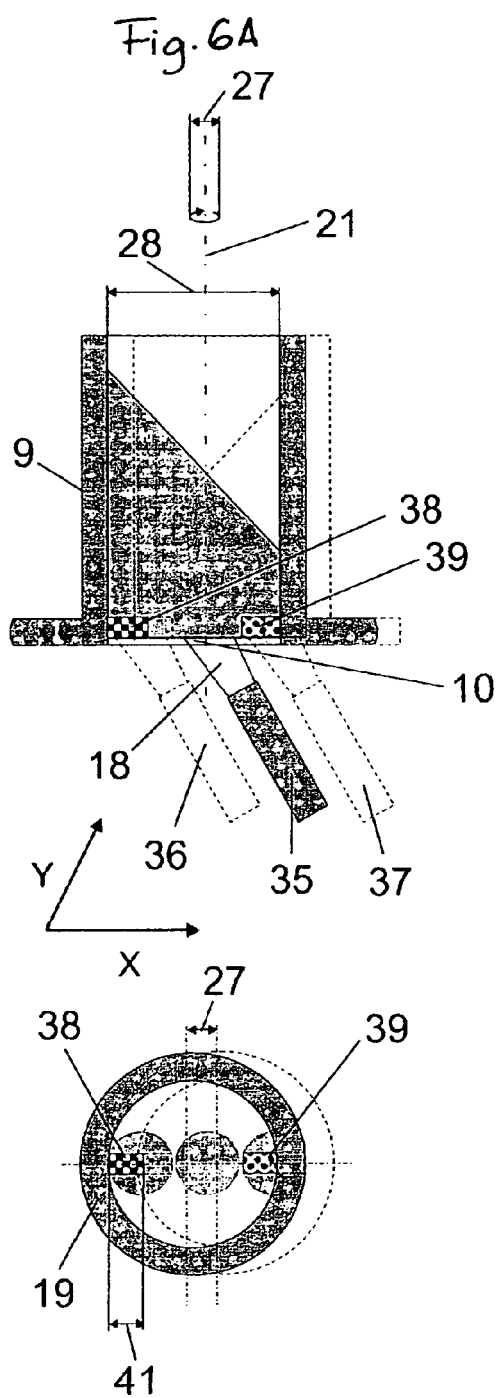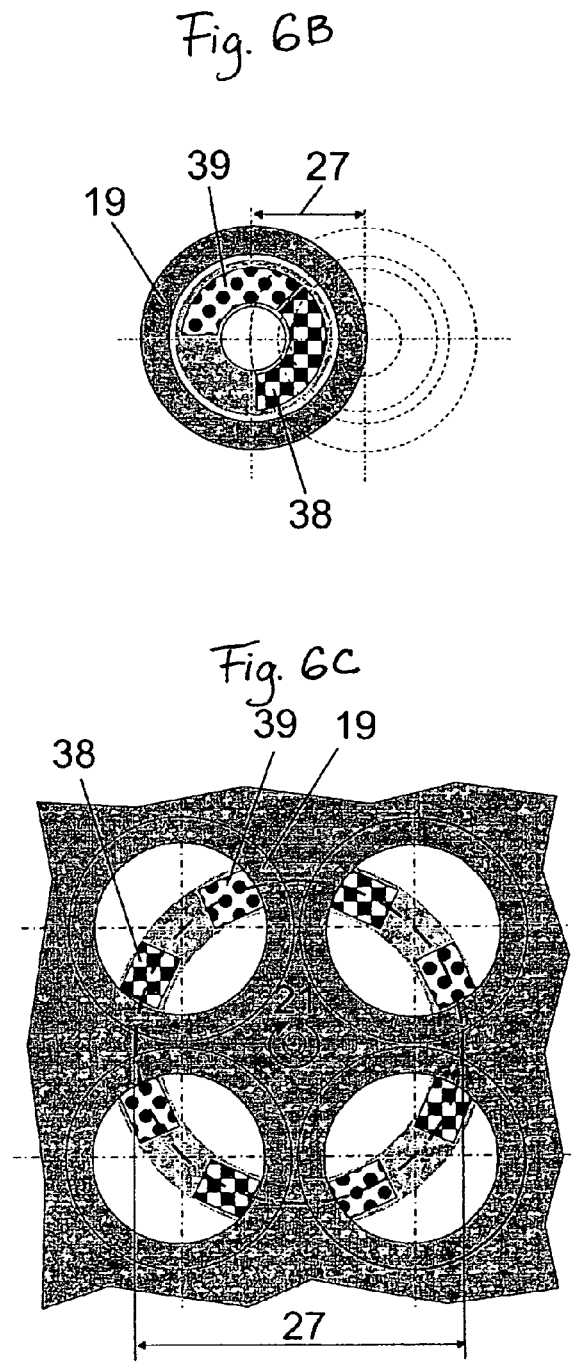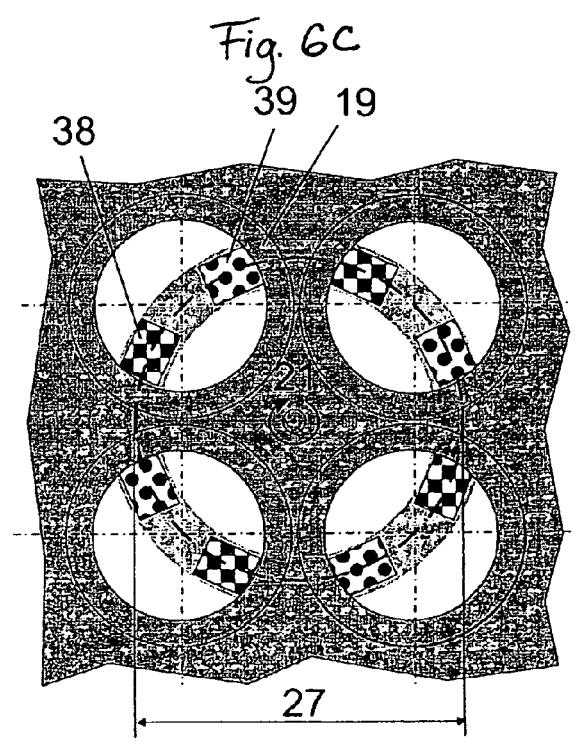

METHOD AND DEVICE FOR RECORDING PROCESS PARAMATERS OF REACTION FLUIDS IN SEVERAL AGITATED MICROREACTORS

PRIORITY CLAIM

This is a U.S. national stage of application No. PCT/EP2005/002928, filed on 18 Mar. 2005. Priority is claimed on the following application(s): Country: Germany, Application No.: 10 2004 017 039.8,Filed: 2 Apr. 2004, the content of which is/are incorporated here by reference.

BACKGROUND OF THE INVENTION

The invention relates to a method and an apparatus for recording of process parameters of reaction liquids in a plurality of microreactors, which are shaken continuously at least until the end of the reaction in all of the microreactors, with the process parameters being recorded in the microreactors during the reaction with the aid of at least one sensor optics device which introduces electromagnetic radiation from a radiation source into the reaction liquid in a microreactor, and with electromagnetic radiation which originates from the reaction liquid in the microreactor being recorded by a sensor which is associated with the radiation source.

The invention is particularly suitable for automated recording of process parameters of microbial, biochemical, enzymatic and chemical reactions in reaction liquids which are shaken without interruption until completion of the reaction in all of the microreactors.

By way of example, the biomass, substrate, product and byproduct concentrations, the self-fluorescence of cells, the fluorescence of fluorescent proteins and amino acids, pH, T, $pO_2$ and $pCO_2$ values, the oxygen transfer rate (OTR) and the carbon-dioxide transfer rate (CTR) can be recorded as parameters of the reaction liquids.

In particular, the above-mentioned parameters are intended to be determined in microreactors with a size of 10 µl-5 ml, in order to reduce the expense for chemical, biochemical, enzymatic and microbial optimization methods, also referred to as screening. Screening is considered, for example, for the core-area selection, media optimization and optimization of process control. The small volumes in the microreactors allow the required high throughputs in many areas of research and development, in particular such as combinational chemistry and molecular biotechnology.

So-called microtiterplate readers are known from the prior art, for recording the absorption and fluorescence in microbial reaction liquids. The shaking movement of the microtiterplates must be interrupted for each recording of process parameters during the reaction. The greater the number of process parameters that are intended to be obtained while the reactions are taking place, the more frequently the shaking movement must be interrupted, thus disturbing mixing processes and substance transport processes. This can result in anaerobic conditions in the case of cultures which cause greater or lesser damage to the various microorganisms. An absorption microtiterplate reader such as this for 200-well microtiterplates for monitoring of microbial growth is available, for example, from the Thermo Electron Corporation, Waltham, Mass., USA. The light absorption by the cells located in the wells is recorded. For this purpose, electromagnetic radiation from a radiation source is introduced into the reaction liquid in the wells, and the electromagnetic radiation emitted from the reaction liquid in the microreactor is recorded by means of a sensor. The sensor signals depend on the layer thickness passed through and on the cell concentration.

Furthermore, U.S. Pat. No. 6,673,532 B2 has already disclosed a microtiterplate reader for recording of the absorption in microbial culture liquids, in which the shaking movement of the microtiterplates need not be interrupted in order to record the absorption during the reaction. By way of example, the known apparatus comprises a microtiterplate with 96 wells, which is held by a microreactor platform. The individual wells have a volume of between 100 µl and 250 µl. At least one sensor optics device is located in a sub-platform arranged under the microreactor platform and has an excitation source, for example a light-emitting diode, as well as a detector, which records the absorption of the electromagnetic radiation from the excitation source in the reaction liquid in the microreactor (wells). The change in the measured absorption indicates a change in the concentration of the analyte in the microreactor. One refinement of the reader provides for the LEDs and the detectors to be moved from one microreactor to another by means of a robot. Another refinement provides for each microreactor to have at least one associated LED and one associated detector within the sub-platform. The sub-platform with the sensor optics device or devices is once again located on a shaking apparatus, which is mounted on a positioning table. The shaking apparatus is a specially manufactured device, in order to allow integration between the positioning table and the sub-platform. The positioning table can be moved in the XY axis direction and is used for the purpose of moving individual microreactors under a dispenser. By way of example, this known apparatus can be used to assess growth conditions for the microorganisms in culture liquids in a valid form, since it avoids the problems which occur as a result of interruption of the shaking movement.

However, the apparatus has the disadvantage of its complex design, particularly that of the shaker, which is specifically matched to the apparatus. A further disadvantage is that the sensor optics device or devices are also shaken in the sub-platform. Owing to the high shaking frequencies and the centrifugal forces associated with them it is possible for problems, and thus errors, to occur in the recording of the process parameters which, in some circumstances, make it necessary to repeat the reaction. This can result in undesirable delays, particularly in the case of series of investigations relating to microbial culture liquids, enzymatic and chemical reactions.

Against the background of this prior art, the invention is bottom on the object of specifying a method for recording of process parameters of reaction liquids in a plurality of microreactors which are shaken continuously during the reaction, and which method operates reliably. A further aim is to specify an apparatus for carrying out the method, which can be provided largely by the use of standard components and apparatuses from biotechnology.

SUMMARY OF THE INVENTION

The solution to this problem is bottom on the discovery that continuous recording of the process parameters is possible even when each sensor optics device is not been moved during the recording of the values of a process parameter, for example during the recording of an instantaneous value of natural fluorescence during the ongoing reaction. The relative movement which occurs during this process between the shaken microreactors and each sensor optics device is without any problems provided that the electromagnetic radiation of each sensor optics device is introduced, during the recording of the process parameters in one of the microreactors, exclusively into this microreactor, and that the radiation which originates from the reaction liquid strikes only the sensor of the associated sensor optics device.

The biomass concentration in one of the microreactors may, for example, be recorded with the aid of scattered light striking the sensor of the sensor optics system, or the radiation which originates from the natural fluorescence of the cells.

The substrate concentration, product concentration and byproduct concentration can be trapped with the aid of IR or Raman spectroscopy. Biotechnological substrates such as glucose or glycerin are IR active and Raman active, and form a specific spectrum, which can be detected even in very complex media. Metabolism byproducts such as acetic acid and ethanol likewise have a characteristic spectrum. Organic substrates can be detected in the microreactors by transmission of the spectrum via optical waveguides to an IR spectrometer or Raman spectrometer. More detailed statements can be found in Sivakesava S., Irudayaraj J., Ali D. (2001): Simultaneous determination of multiple components in lactic acid fermentation using FT-MIR, NIR, and FT-Raman spectroscopic techniques, Process Biochemistry 37, 371-378.

In one advantageous refinement of the invention, the reaction liquids in the microreactors have at least one chemical sensor material, in particular such as a fluorescent dye which, in particular, can be immobilized on at least one inner wall of the microreactor. Fluorescent dyes react specifically to their environmental conditions. For example, platinum porphyrins or ruthenium complexes react to the presence of oxygen by cancellation of their fluorescence characteristics. Fluorescence indicator solutions likewise have a sensitive reaction to changes in the dissolved $CO_2$ concentration ($pCO_2$) and of the pH value by changing their fluorescence characteristics. If these substances are immobilized in a porous polymer matrix or are dissolved or suspended in the reaction liquid, then they act as optical sensors (also referred to as optodes) for pH, T, $PO_2$, $pCO_2$ values (Liebsch (2000): Time Resolved Luminescence Lifetime Imaging with Optical Chemical Sensors, Dissertation at Regensburg University). However, it is also possible to use normally dissolved pH indicators.

BRIEF DESCRIPTION OF THE DRAWINGS

The invention will be explained in more detail in the following text with reference to the figures, in which:

FIGS. 6A-6C are schematic diagrams illustrating a third variant of the method according to the invention using chemical sensors.

DETAILED DESCRIPTION OF THE PREFERRED EMBODIMENTS

Figure 1A:
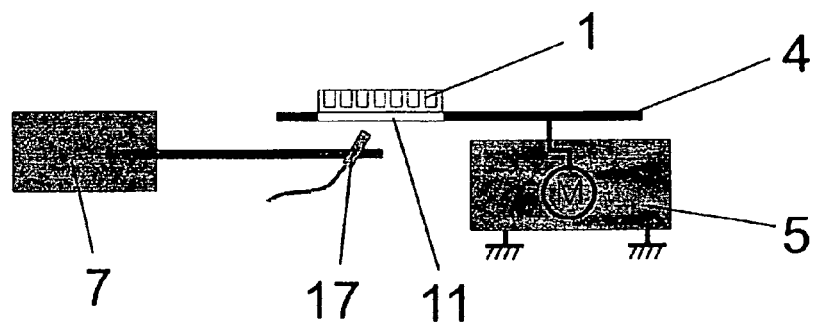
FIGS. 1A-C show three variants of preferred apparatuses for carrying out the method according to the invention.

A microtiterplate (1) with an array of microreactors is inserted into a holder in a tray (4) of a rotation shaker (5, 6). The rotation shaker (5, 6) reaches a maximum shaking frequency of, for example 500-2000 µm. The shaking diameter of the rotation shaker is matched to the recording process.

Electromagnetic radiation at a wavelength of 200 nm-25 µm is introduced via a sensor optics device (17) through the cutout (11) in the tray (4) into those wells of the microtiterplate (1) which are permeable to the radiation, and the radiation emerging from the wells is recorded by the sensor optics device (17).

FIG. 1A shows one embodiment with a stationary rotation shaker (5), in which the subarea of the tray (4) on which the microtiterplate (1) is fitted projects beyond the drive. This ensures free access between the sensor optics device (17), which is arranged on an X/Y positioning unit (7), and the microtiterplate (1) from its lower face.

Figure 1B:
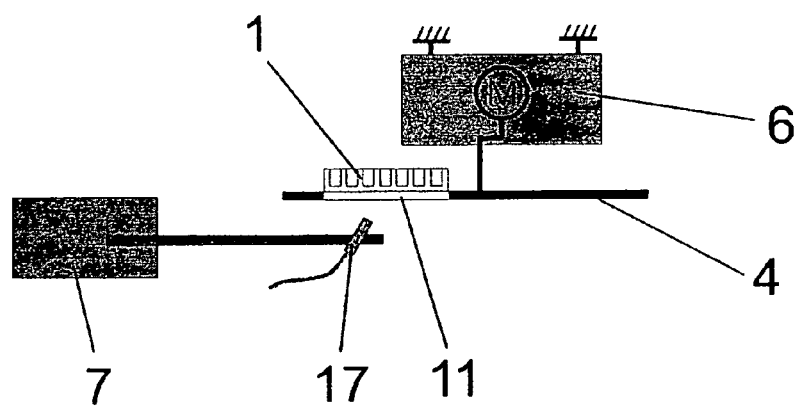

FIG. 1B shows an embodiment with a tray (4) which is driven by a suspended rotation shaker (6). That part of the tray (4) to which the microtiterplate (1) is fitted need project beyond the rotation shaker (6) in this embodiment only when the wells are also intended to be accessible from above.

Figure 1C:
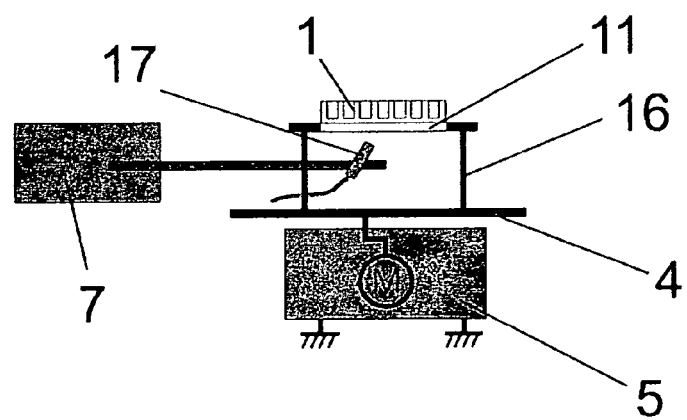

FIG. 1C shows an embodiment in which the microtiterplate (1) is held by a shaking frame (16) with a cutout (11). The shaking frame (16) is separated from the microtiterplate (1) in the vertical direction by the planar tray (4). Because the shaking frame (16) is designed to be open at the side, the sensor optics device (17) can be moved under each well in the microtiterplate by means of the X/Y positioning unit (7) without being impeded from the side.

Figure 2A:
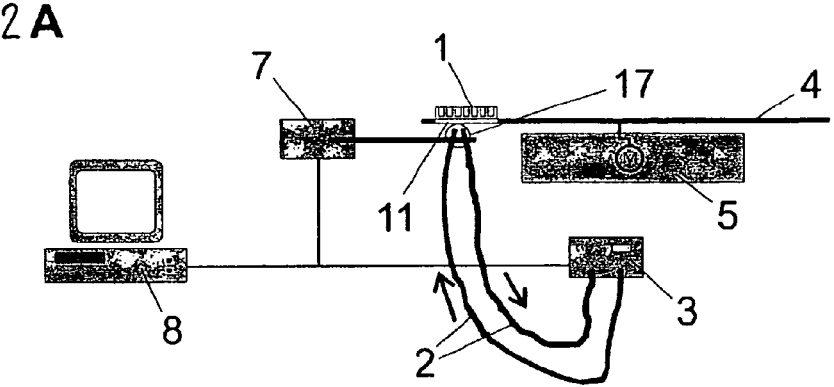
FIGS. 2A-C show various embodiments of a sensor optics device for the apparatus according to the invention.
Figure 2B:
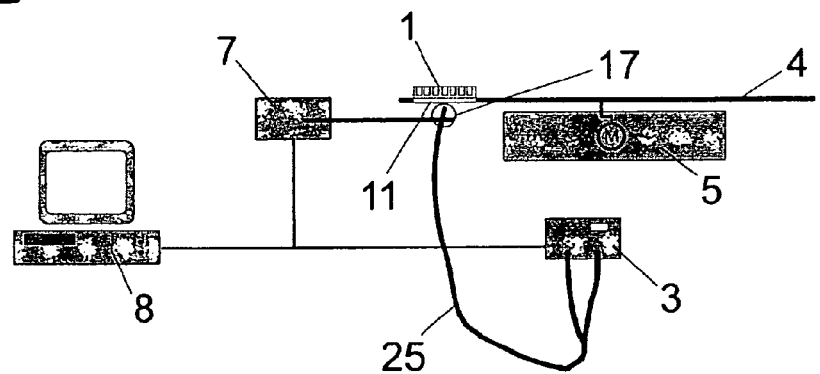

FIGS. 2A, 2B show apparatuses in which the electromagnetic radiation from the radiation source and the radiation originating from the reaction liquids are passed via optical waveguides (2, 25).

The variant in FIG. 2A shows the radiation being carried separately via two optical waveguides (2). The radiation is introduced via one optical waveguide (2) which leads towards the reactor, and the radiation originating from the microreactor is carried via an optical waveguide (2) which leads away from the microreactor. A radiation source that feeds the sensor optics device, and a sensor, are located in a reader (3).

The variant shown in FIG. 2B differs from the variant shown in FIG. 2A only in that the two optical waveguides (2) are combined in one Y-optical waveguide (25). The optical waveguides are composed of individual optical fibers or else of optical fiber bundles. The sensor and the radiation source which feeds the sensor optics device are located in the reader (3).

Figure 2C:
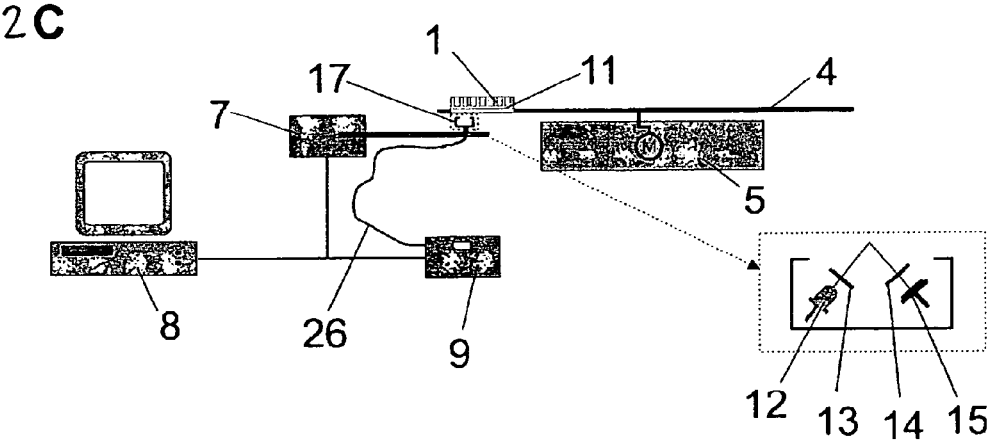

FIG. 2C shows a sensor optics device (17) without any optical waveguides. The radiation source (12) and the sensor (15) are located directly in the sensor optics device (17), which may additionally have filters 13, 14 in the beam path. The excitation light from the radiation source (12) is aligned directly with each individual microreactor, while the reaction-dependent radiation which originates from the reaction liquid in the microreactor strikes the sensor (15). The sensor optics device (17) is connected to an electronic circuit (9) via a cable or cables (26) in order to supply the radiation source (12) and in order to transmit the sensor signals. The circuit (9) controls the radiation source (12) and is used for reading the sensor signals. In all variants, the data is acquired and evaluated by means of a data processing unit, for example a computer (8). In the variants shown in FIGS. 2A, B, the functionality of the electronic circuit (9) is integrated in the reader (3). The sensor optics device (17) is attached to the arm of an X-Y positioning unit (7), in all of the variants. The X-Y positioning unit (7) is likewise driven by the computer (8), by means of a control software.

Depending on the requirement for the measurement task, it is possible to inject electromagnetic radiation in a closely constrained wavelength range, for example produced via optical filters 13, diffraction gratings, prisms or directly by a radiation source with a defined spectrum, such as a laser or an LED, and to supply the sensor only with specific wavelengths from the emitted light. The emitted light can likewise be filtered by means of optical filters 14, diffraction gratings or prisms for this purpose.

If a flashlamp is used to excite the analytes in the reaction liquid of a microreactor, it is advantageous for the shaking rotation speed of the rotation shaker (5, 6) and the pulse repetition frequency of the flashlamp to be matched such that no beat states occur. Beat states occur when the light flashes strike a small number of positions on the bottom of the reactor and the positions move on the bottom of the reactor as a result of lack of synchronization between the shaker frequency and the flash frequency. The microreactor which is illustrated in FIG. 4 and is bounded by a circular-cylindrical bottom (10) and a cylindrical casing (19), rotates with a fixed shaking diameter over a fixed-position light beam (18) of the sensor optics device (17). The rotation of the microreactor results in the light beam (18) describing a circular line (31) on the bottom (10) of the microreactor (see FIGS. 3A and 3B).

Figure 3A:
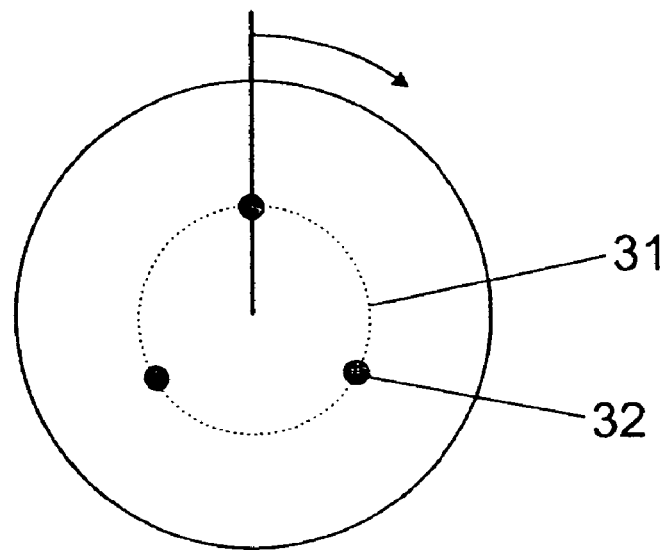
FIGS. 3A-B show two schematic plan views of a cylindrical microreactor which rotates with a fixed shaking diameter over a light beam of a flashlamp.
Figure 4:
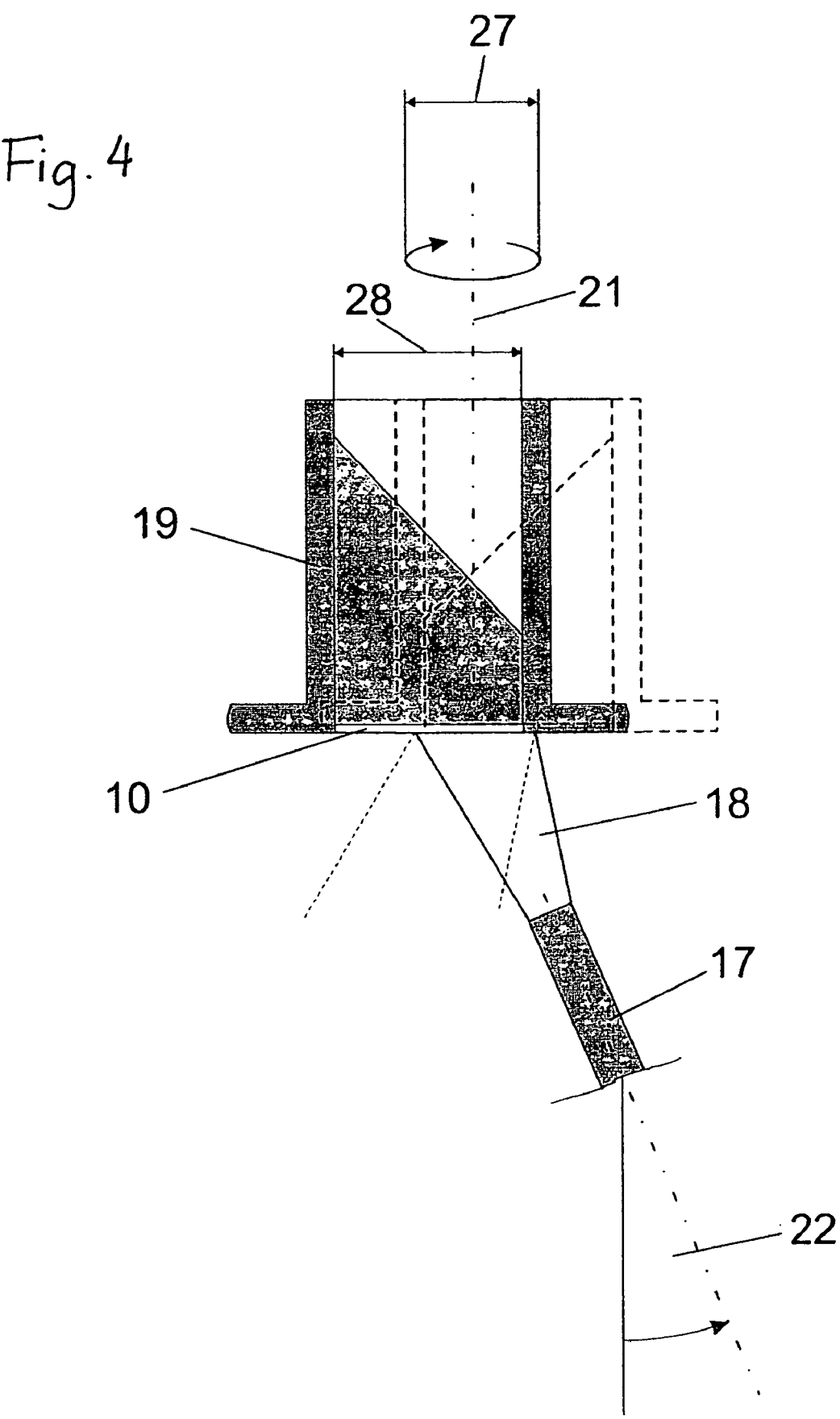
FIG. 4 is a schematic diagram illustrating a first variant of the method according to the invention.

FIG. 3A illustrates a state in which only 3 flashes are distributed over the circumference of the circular line (31), as a result of the choice of the shaking rotation speed (n) and of the flash frequency ($f_a$) of the flashlamp. In this case, $f_a=3*n$, so that only 3 flashes are initiated per revolution. Beat states occur particularly if the flash frequency ($f_a$) is a natural multiple of the shaking rotation speed (n). In this case, the light flashes initially start at the same positions (32) on the circular line (31). If the coverage of the circular line (31) with flashes is low (<4 flashes/circular line) and the start of the flashes is not synchronized with the liquid movement in the reactor, the positions (32) move in the clockwise sense or counterclockwise sense on the circular line (31). Because of the angle (22) of the sensor optics device (17), this leads to different intensities of the electromagnetic radiation emitted from the microreactor, and disadvantageous oscillations of the measurement signal can thus occur.

Figure 3B:
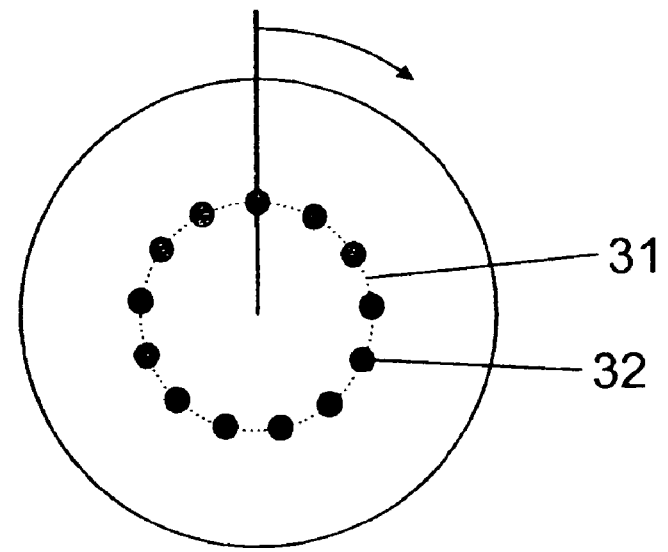

A greater number of light flashes is therefore desirable in order to avoid beat states, with these being distributed uniformly over the circular line 31. This can be achieved by satisfying the condition $f_a=N*n$ (where N=natural number). FIG. 3B illustrates one example relating to this. Thirteen light flashes are shown over the circumference of the circular line (31). The light flashes can be emitted during one revolution, or else during a plurality of revolutions, of the rotation shaker. The relationship $n=f_a*P/U$ (where P=number of flashes on the circular line and U=number of revolutions before P is reached) results in the operational conditions being set such that as high a number of flashes (P>10) as possible are distributed over the circumference of the circular line. This makes it possible to obtain a stable and homogeneous sensor signal in order to record the process parameters in the microreactor.

A further possible way to stabilize the sensor signal is to synchronize the flashes from the radiation source with the shaking drive, and thus with the liquid movement in the microreactors. The position of the tray (4) with respect to the sensor optics device (17) can be determined at any time by means of a position sensor (for example a light barrier, an acceleration sensor or a Hall sensor). The light flashes from the flashlamp are triggered taking into account the position information. The flash is preferably triggered when the reaction liquid which is sloshing in the centrifugal acceleration direction is located above the sensor optics device (17). This prevents the light beam (18) from striking zones of the microreactor in which no reaction liquid, or only a very small amount of reaction liquid, is located temporarily because of the centrifugal acceleration.

The method according to the invention for recording of the process parameters of reaction liquids will be explained in more detail in the following text, on the basis of two different variants, by means of an apparatus as shown in FIG. 2.

FIG. 4 illustrates one method for successive recording of the values of process parameters in each case only one microreactor, with the sensor optics device (17) subsequently being moved by means of the positioning unit (7).

The sensor optics device (17) is aligned under one microreactor in such a manner that the electromagnetic radiation, at a wavelength between 200 nm-25 µm, is introduced exclusively into this microreactor in the form of the light beam (18) for recording of individual measured values during the reaction. If a cylindrical microreactor is used having a circular-cylindrical bottom (10), the shaking diameter (27) of the rotation shaker (5, 6) about the eccentric axis (21) (see FIG. 4) is chosen such that the light beam (18) from the sensor optics device (17) strikes only the bottom (10) of one of the microreactors. For this purpose, the shaking diameter (27) must be chosen to be less than or equal to the diameter (28) of the bottom (10).

In the case of reactions which take place quickly, it is possible in order to speed up the recording process to combine groups of microreactors in a microreactor array, with the process parameters of the individual groups being recorded successively, but with the process parameters in the microreactors in one group being recorded at the same time by one sensor optics device (17) for each microreactor in the group. The sensor optics devices for simultaneous recording within one group are arranged on the positioning unit (7). After simultaneous recording of the process parameters in the microreactors in one group, the sensor optics devices are moved to the next group. The sensor optics devices for one group are aligned under the microreactors in that group in such a manner that the electromagnetic radiation of each sensor optics device for the recording of individual measured values is introduced exclusively into that microreactor under which the sensor optics device is currently located.

In order to avoid signal flooding of the sensor, for example of a photodetector, by light reflections of the excitation light on the bottom (10), each sensor optics device is aligned with respect to each microreactor in such a way that none of the electromagnetic radiation which is reflected from the walls, in particular the bottom (10) of the microreactor, strikes the sensor. For this purpose, the optical waveguide end which is used as the sensor optics device (17) is positioned at an acute angle (22) with respect to a perpendicular to the bottom (10) of the microreactor. Different optimal positioning angles (22) are used, depending on the numerical aperture of the optical waveguide, preferably between 25° and 40°.

Instead of successive recording of the process parameters it is, however, also possible to record the process parameters in all of the microreactors at the same time by one sensor optics device for each microreactor. The sensor optics devices are aligned under the microreactors in such a manner that the electromagnetic radiation (200 nm-25 µm) is introduced exclusively into that microreactor which is associated with that sensor optics device, in the form of the light beam (18) for recording of the measured values during the reaction.

Figure 5A:
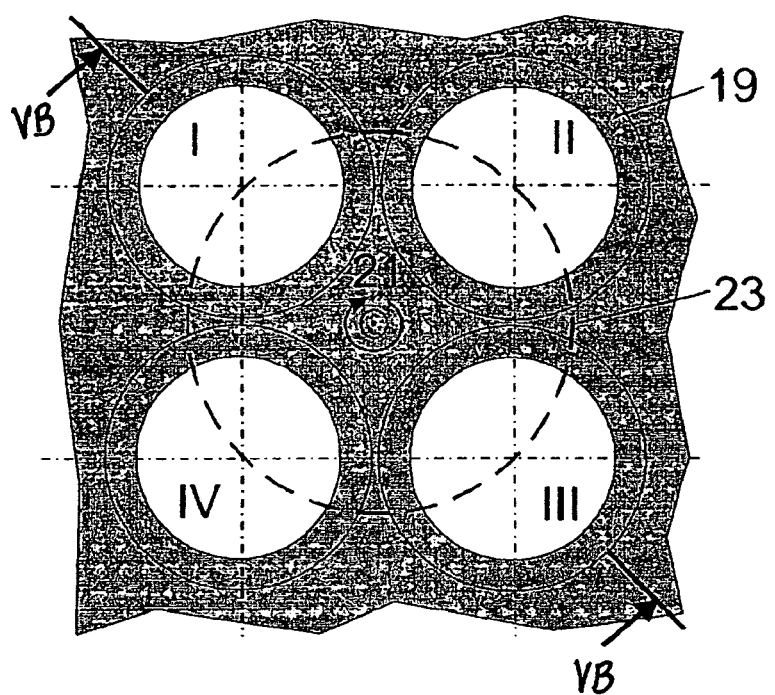
FIGS. 5A and 5B is a schematic diagrams illustrating a second variant of the method according to the invention.
Figure 5B:
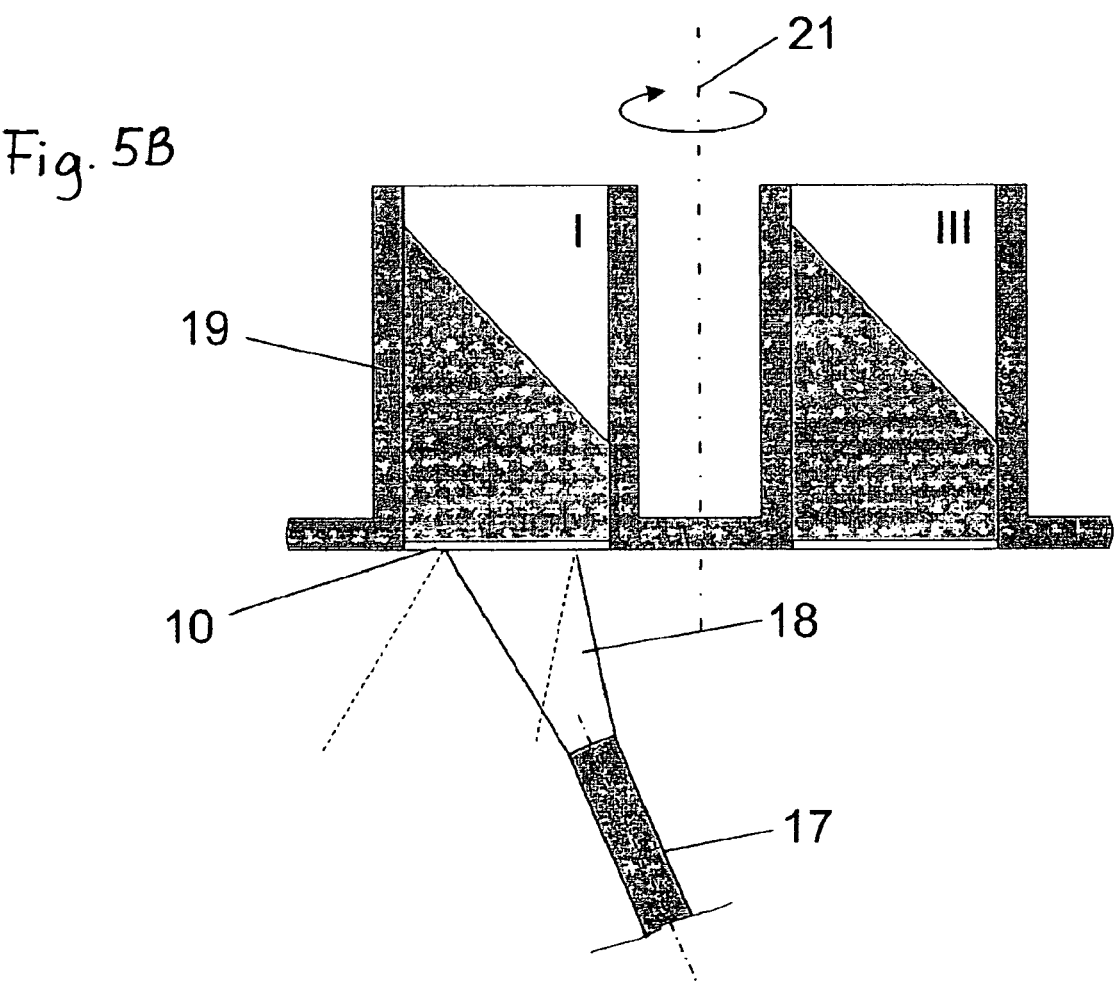

FIG. 5 illustrates one method for successive recording of the process parameters in four microreactors which are arranged adjacent to one another. The process parameters of the microreactors are recorded by the stationary sensor optics device (17) successively, on the basis of the relative circular movement with respect to this sensor optics device (17). The electromagnetic radiation of the sensor optics device (17) is introduced, during the recording of the process parameters in one of the four microreactors, exclusively into this microreactor. The radiation which emerges from the reaction liquid strikes exclusively that sensor of the sensor optics device (17). Simultaneous injection into two adjacent microreactors is avoided because of the arrangement of the sensor optics device (17) with respect to the bottom (10) of the microreactors.

The sensor optics device (17) is aligned with one of the four microreactors. If the shaking diameter is chosen to be equal to the diagonal distance between the center points of the microreactors, with the microreactors being distributed as illustrated on the tray (4), then the 4 microreactors circle successively over the light beam (18) of the sensor optics device (17) during one revolution. The microreactors are moved over the sensor optics device (17) in the sequence I-IV, with the light beam (10), which is in a fixed position during the recording process, describing a circular line (23). The sensor signals which are caused by the individual microreactors are recorded by means of the computer (8), which is not illustrated here. In the course of the evaluation of the sensor signals, those sensor signals and microreactors from which the electromagnetic radiation which is responsible for the sensor signals originates are associated with one another. The microreactor position information that is required for the association process can be recorded, for example, by means of a position sensor (for example a light barrier, an acceleration sensor or a Hall sensor) which is arranged on the rotation shaker (5, 6).

If the microtiterplate (1) has more than four microreactors as illustrated in FIG. 5, the sensor optics device (17) is moved to a next adjacent group of microreactors (which are arranged such that they match one another) with four microreactors, after recording of the process parameters for the first group of four microreactors by the positioning unit (7). A positioning angle of the sensor optics device (17) at an angle (22) of between 25° and 40° with respect to bottom (10) of the microreactors has also been found to be advantageous for this method.

However, the method which has been explained in principle with reference to FIG. 5 can also be used to record the process parameters of a greater number (>4) of microreactors per group. The shaking diameter (27) must then be chosen such that the microreactors describe a circle around the fixed-position sensor optics device, in which more than four microreactors are recorded successively during one revolution.

In order to speed up the recording process, it is possible in a method as shown in FIG. 5 or FIG. 6C for the process parameters of a plurality of groups of microreactors arranged adjacent to one another to each be recorded in parallel by one sensor optics device for each group.

According to the invention, the reaction liquids in the microreactors may have at least one chemical sensor material, which is preferably applied to at least one inner wall of the microreactor, for example to the bottom (10). Chemical sensors such as these are, for example, fluorescent dyes which act as indicators of process parameters such as pH, T, $pO_2$ and $pCO_2$. In dissolved form, the fluorescent dyes can be used to determine the process parameters using the apparatuses and method as described with reference to FIGS. 1-5. If the fluorescent dyes are immobilized on the inner walls as sensitive layers (38, 39), a specific alignment of the sensor optics device (17) is required, as is illustrated by way of example in FIG. 6A-B for the measurement method shown in FIG. 4.

In this case, a plurality of sensitive layers (38, 39) can be arranged on the bottom (10) of the microreactor in such a way that different process parameters can be recorded. A cutout in the transparent bottom (10) is left free in order that the light beam (18) can also enter the liquid volume without any impediment. As shown in FIG. 6A, the alignment of the sensor optics device (17) and the shaking diameter (27) is to be matched such that the light beam (18) always strikes the sensitive layer (38, 39) or the cutout between them during one revolution of the tray (4) (shaking diameter (27)<[reactor diameter (28)/(number of sensitive layers (N)+1)−length of the sensitive layer (41)]). As is illustrated in 41, the length of a sensitive layer in this case means the longest geometric dimension of a sensitive layer (38, 39). With regard to the recording of the measured values, it follows from this that the sensor optics device (17) is moved to different positions 35, 36 and 37 underneath the bottom (10) of the microreactor with the aid of the XY positioning unit (7), in order to record different process parameters. Position 35 is used to record the natural fluorescence or the stray light of the reaction liquid, while positions 36, 37 are used to record the emission from the various sensitive layers 38, 39.

In the variant shown in FIG. 6B, the various process parameters are recorded in a microreactor without changing the position of the sensor optics device between two recording processes. In this case, the light beam (18) successively strikes the sensitive layers (38, 39), which are immobilized on the bottom, on a circular path. A part of the bottom surface is free in order to allow direct injection into the reaction liquid, as is required for example for recording of specific process parameters, such as the stray light intensity or natural fluorescence of the reaction liquid. The various sensor signals are associated throughout the rotation of the microreactor by means of a position sensor, which is not illustrated.

In the variant shown in FIG. 6C, the sensitive layers (38, 39) are fitted in the microreactors such that a plurality of microreactors are recorded successively by the light beam (18) during one revolution of the tray. The surface (40) which is covered by the sensor optics device (17) records four microreactors and different process parameters, which must be associated with the individual microreactors after the recording of the signals. In this case, this is once again done by means of a position sensor. If the microreactor array comprises more than the four illustrated microreactors, the sensor optics device is moved by the positioning unit (7) to further groups of microreactors, which are each arranged adjacent to one another and each have four microreactors, after recording the process parameters for the first group of four microreactors.

When microreactors are used to cultivate microorganisms, they preferably have an upper opening which can be covered with a gas-permeable cover during operation, for example in the form a self-adhesive membrane. This membrane allows monoseptic operation of the microreactors. The reaction which takes place in the reaction liquid is supplied with the necessary gaseous reaction component, but is not impeded by gaseous reaction products.

Figure 7:
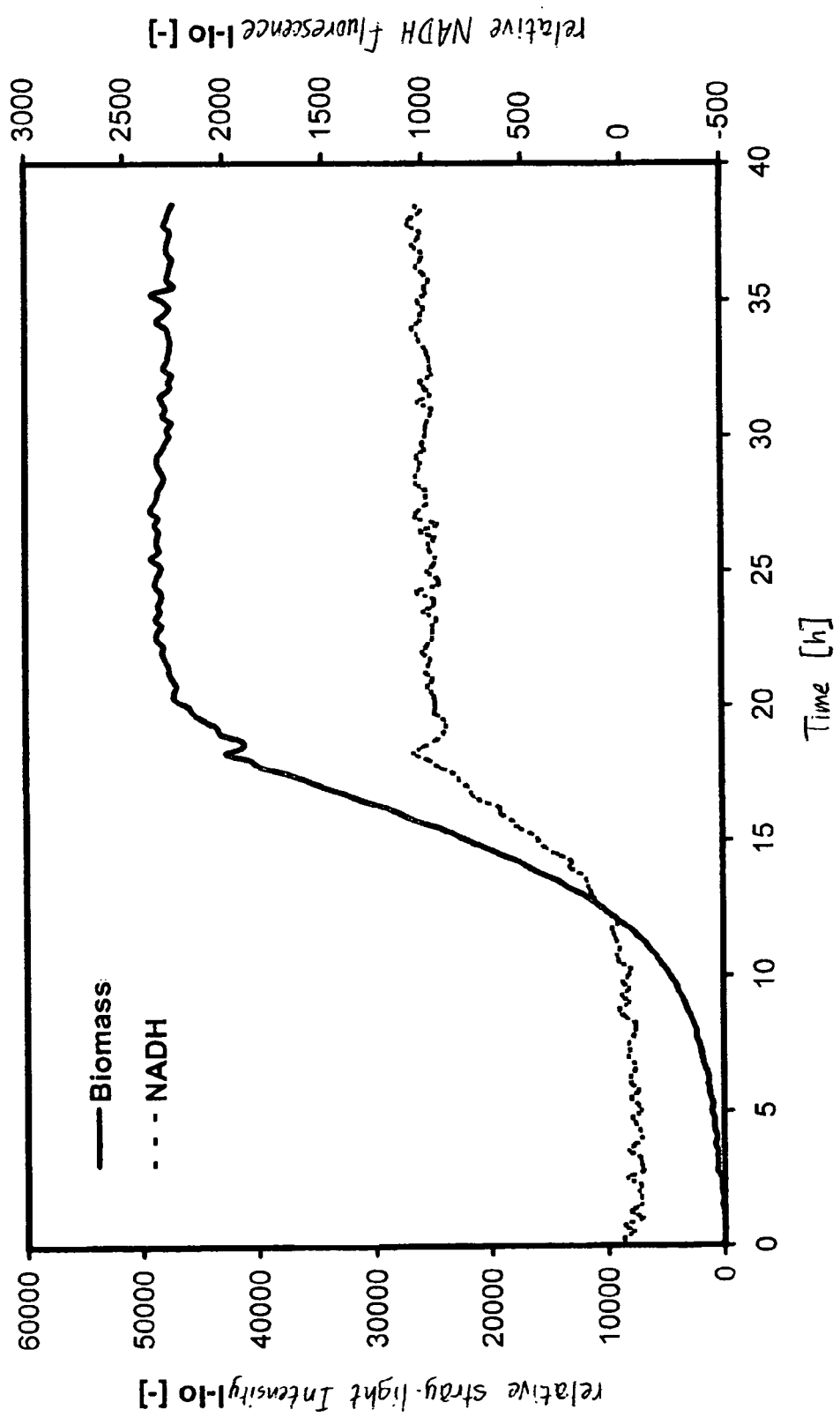
FIG. 7 is a graph exhibiting measurement curves of a culture of Hansenula polymorpha.

An one example of the recording of process parameters which have been determined using the method according to the invention, FIG. 7 shows measurement curves for a *Hansenula polymorpha* wt in 2xYP-medium (Yeast-Peptone) culture with 10 g/L glycerin at a temperature of 27° C. The process parameters that were observed were the relative stray light intensity (at 620 nm) and the relative NADH fluorescence (excited at 340 nm, emission at 460 nm) of the culture throughout the duration of the reaction. The individual process parameters were recorded using a Y optical waveguide with a positioning angle of 30° and at a distance of 1 mm from the microtiterplate bottom. The shaking frequency in this case corresponded to 995 rpm, and the shaking diameter (27) was 3 mm. The reaction was carried out using a conventional 48-well microtiterplate (Greiner Bio-one, Frickenhausen, Part No.: 677 102) and a filling volume of 600 µl. A gas-permeable adhesive film was used as a cover (Abgene, Hamburg, Part No.: AB-0718), in order to cover the 48-well microtiterplate.

What is claimed is:

1. A method for recording process parameters of reaction liquids in a plurality of microreactors, comprising the steps of:
   continuously shaking, by a rotation shaker, a plurality of microreactors in a shaking diameter less than a diameter of a bottom surface of each of the microreactors until the end of the reactions in all of the microreactors;
   introducing electromagnetic radiation into a reaction liquid in only one of the microreactors using a radiation source of a sensor optics device disposed on a positioning unit;
   recording processing parameters of the reaction liquid by recording emitted electromagnetic radiation which originates only from the reaction liquid in the one of the microreactors using a sensor of the sensor optics device associated with the radiation source, the sensor optics device being held stationary under the one of the microreactors during said steps of introducing and recording so that the shaking microreactors move relative to the sensor optics device;
   successively performing the steps of introducing and recording for each of the plurality of microreactors including moving the sensor optics device with the positioning unit to a next successive one of the microreactors after the completion of each said step of recording.

2. The method of claim 1, wherein the radiation source is a flashlamp, and the method further comprises the step of matching a pulse repetition frequency of the light flashes produced by the flashlamp to the shaking movement of the plurality of microreactors such that the light flashes strike the one of the microreactors at at least four different points.

3. The method of claim 1, wherein the radiation source is a flashlamp, and the method further comprises the step of matching a pulse repetition frequency of the light flashes produced by the flashlamp is matched to the shaking movement of the plurality of microreactors such that the light flashes always strike the microreactor at the same point during the shaking movement.

4. The method of claim 1, wherein at least one of the electromagnetic radiation from the radiation source and the radiation which originates from the reaction liquids is passed through optical waveguides.

5. The method of claim 1, wherein the sensor optics device is aligned with respect to the one of the microreactors such that none of the electromagnetic radiation which is reflected from the walls of the microreactor strikes the sensor.

6. The method of claim 1, wherein the reaction liquids in the microreactors have at least one chemical sensor material.

7. The method of claim 6, wherein the chemical sensor material is applied to at least one inner surface of the microreactor.

8. A method for recording process parameters of reaction liquids in microreactors, comprising the steps of:
   continuously shaking, by a rotation shaker, the plurality of microreactors in a shaking diameter less than a diameter of a bottom surface of each of the microreactors until the end of the reactions in all of the microreactors;
   introducing electromagnetic radiation into a reaction liquid in only a group of at least two of the microreactors using respective radiation sources of at least two sensor optics devices;
   recording processing parameters of the reaction liquids by recording emitted electromagnetic radiation which originates only from the reaction liquids in the at least two microreactors using respective sensors of the at least two sensor optics devices associated with the radiation sources, the at least two sensor optics devices being held still under the at least two microreactors during said steps of introducing and recording so that the shaking microreactors move relative to said sensor optics device.

9. The method of claim 8, further comprising successively performing the steps of introducing and recording for different groups of the plurality of microreactors including moving the sensor optics devices to a next successive one of the groups of microreactors after the completion of each said step of recording.

10. The method of claim 8, wherein the radiation source is a flashlamp, and the method further comprises the step of matching a pulse repetition frequency of the light flashes produced by the flashlamp to the shaking movement of the plurality of microreactors such that the light flashes strike the one of the microreactors at at least four different points.

11. The method of claim 8, wherein the radiation source is a flashlamp, and the method further comprises the step of matching a pulse repetition frequency of the light flashes produced by the flashlamp is matched to the shaking movement of the plurality of microreactors such that the light flashes always strike the microreactor at the same point during the shaking movement.

12. The method of claim 8, wherein at least one of the electromagnetic radiation from the radiation source and the radiation which originates from the reaction liquids is passed through optical waveguides.

13. The method of claim 8, wherein the sensor optics devices are aligned with respect to the microreactors such that none of the electromagnetic radiation which is reflected from the walls of the microreactor strikes the sensor of the sensor optics devices.

14. The method of claim 8, wherein the reaction liquids in the microreactors have at least one chemical sensor material.

15. The method of claim 14, wherein the chemical sensor material is applied to at least one inner surface of the microreactor.

16. A method for recording process parameters of reaction liquids in microreactors, comprising the steps of:
   continuously shaking, by a rotation shaker, the plurality of microreactors until the end of the reactions in all of the microreactors;
   introducing electromagnetic radiation into a reaction liquid in only one microreactor of a first group of at least two of the microreactors using a radiation source of a sensor optics device;
   recording processing parameters of the reaction liquids by recording emitted electromagnetic radiation which originates only from the reaction liquids in the one microreactor using a sensor of the sensor optics device associated with the radiation source, the sensor optics device being held stationary under the one microreactor during said steps of introducing and recording so that the shaking microreactors move relative to said sensor optics device,
   wherein a shaking diameter of the rotation shaker is tuned such that the steps of introducing and recording for each of the at least two microreactors, including moving the first group of at least two microreactors after the completion of each said step of recording, are successively performed during one revolution of the rotation shaker such that the steps of introducing and recording are performed on each of the at least two microreactors of the first group without moving the sensor optics device.

17. The method of claim 16, further comprising:
moving said sensor optics device to a second group of microreactors after performing said steps of introducing and recording for each of the microreactors in the first group of at least two microreactors; and
performing the steps of introducing and recording for each of the microreactors in the second group.

18. The method of claim 16, wherein a plurality of groups of microreactors which are arranged adjacent to one another are recorded in parallel by respective sensor optics devices.

19. The method of claim 16, wherein the radiation source is a flashlamp, and the method further comprises the step of matching a pulse repetition frequency of the light flashes produced by the flashlamp to the shaking movement of the plurality of microreactors such that the light flashes strike the one of the microreactors at at least four different points.

20. The method of claim 16, wherein the radiation source is a flashlamp, and the method further comprises the step of matching a pulse repetition frequency of the light flashes produced by the flashlamp is matched to the shaking movement of the plurality of microreactors such that the light flashes always strike the microreactor at the same point during the shaking movement.

21. The method of claim 16, wherein at least one of the electromagnetic radiation from the radiation source and the radiation which originates from the reaction liquids is passed through optical waveguides.

22. The method of claim 16, wherein the sensor optics device is aligned with respect to the one of the microreactors such that none of the electromagnetic radiation which is reflected from the walls of the microreactor strikes the sensor.

23. The method of claim 16, wherein the reaction liquids in the microreactors have at least one chemical sensor material.

24. The method of claim 23, wherein the chemical sensor material is applied to at least one inner surface of the microreactor.

25. An apparatus for recording process parameters of reaction liquids in microreactors, comprising:
a microreactor platform comprising a tray for holding a microtiter plate having
at least two microreactors which are at least partially permeable for electromagnetic radiation, said microreactor platform being substantially planar and at least partially permeable for electromagnetic radiation in the area of bottom surfaces of said microreactors;
a shaking device comprising a rotation shaker connected to said microreactor platform for shaking the microreactor platform in a shaking movement, wherein a shaking diameter of each of the microreactors is less than a diameter of the bottom surface of each of the microreactors;
at least one sensor optics device decoupled from the shaking movement of the microreactor platform and having a sensor and a radiation source, said radiation source introducing electromagnetic radiation into the reaction liquid of one of said microreactors, and said sensor which is associated with said radiation source detecting electromagnetic radiation originating from said reaction liquid in said one of said microreactors;
a data processing unit connected to said sensor for recording and evaluating the sensor signals; and
a positioning unit mounted in a fixed position with respect to the microreactor platform and connected to said at least one sensor optics device for moving said at least one sensor optics device under said bottom surfaces of said microreactors.

* * * * *